(12) United States Patent
Eckhardt

(10) Patent No.: US 8,092,534 B2
(45) Date of Patent: Jan. 10, 2012

(54) REVISION DEVICE

(75) Inventor: Jason Eckhardt, Memphis, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 986 days.

(21) Appl. No.: 11/560,395

(22) Filed: Nov. 16, 2006

(65) Prior Publication Data

US 2008/0119934 A1 May 22, 2008

(51) Int. Cl.
*A61F 2/44* (2006.01)
(52) U.S. Cl. ................................ 623/17.11
(58) Field of Classification Search ............... 606/86 R; 623/17.11–17.16

See application file for complete search history.

(56) References Cited

U.S. PATENT DOCUMENTS

| | | | |
|---|---|---|---|
| 4,759,769 A | 7/1988 | Hedman et al. | |
| 5,314,477 A | 5/1994 | Marnay | |
| 5,458,642 A | 10/1995 | Beer et al. | |
| 5,507,816 A | 4/1996 | Bullivant | |
| 5,571,109 A * | 11/1996 | Bertagnoli | 606/86 A |
| 5,674,296 A * | 10/1997 | Bryan et al. | 623/17.16 |
| 5,702,454 A | 12/1997 | Baumgartner | |
| 5,755,797 A | 5/1998 | Baumgartner | |
| 5,782,832 A | 7/1998 | Larsen et al. | |
| 5,827,328 A | 10/1998 | Buttermann | |
| 5,865,845 A | 2/1999 | Thalgott | |
| 5,888,226 A | 3/1999 | Rogozinski | |
| 5,895,428 A | 4/1999 | Berry | |
| 6,063,121 A | 5/2000 | Xavier et al. | |
| 6,740,118 B2 | 5/2004 | Eisermann et al. | |
| 7,235,105 B2 * | 6/2007 | Jackson | 623/17.16 |
| 7,517,363 B2 * | 4/2009 | Rogers et al. | 623/17.11 |
| 7,549,995 B2 * | 6/2009 | Schultz | 606/99 |
| 2002/0138146 A1 * | 9/2002 | Jackson | 623/17.15 |
| 2002/0156528 A1 | 10/2002 | Gau | |
| 2002/0169508 A1 * | 11/2002 | Songer et al. | 623/17.11 |
| 2004/0002759 A1 | 1/2004 | Ferree | |
| 2004/0002761 A1 * | 1/2004 | Rogers et al. | 623/17.13 |
| 2004/0220670 A1 | 11/2004 | Eisermann et al. | |
| 2004/0230307 A1 | 11/2004 | Eisermann | |
| 2005/0203626 A1 * | 9/2005 | Sears et al. | 623/17.11 |
| 2007/0021837 A1 * | 1/2007 | Ashman | 623/17.16 |
| 2007/0185578 A1 * | 8/2007 | O'Neil et al. | 623/17.14 |
| 2007/0203581 A1 * | 8/2007 | Vanaclocha | 623/17.14 |
| 2007/0233261 A1 * | 10/2007 | Lopez et al. | 623/17.13 |

FOREIGN PATENT DOCUMENTS

| | | |
|---|---|---|
| WO | WO 97/23175 | 7/1997 |
| WO | WO 00/42954 | 7/2000 |
| WO | WO 01/01893 | 1/2001 |
| WO | WO 01/19295 | 3/2001 |
| WO | WO 02/30337 | 4/2002 |
| WO | WO 03/094806 | 11/2003 |
| WO | WO 2004016217 | 2/2004 |

OTHER PUBLICATIONS

Unpublished U.S. Appl. No. 11/467,355, filed Aug. 25, 2006 titled "Revision Spacer".
Unpublished U.S. Appl. No. 11/411,751, filed Apr. 26, 2006 titled "Revision Fixation Plate and Method of Use".

* cited by examiner

*Primary Examiner* — Eduardo C Robert
*Assistant Examiner* — Steven Cotroneo

(57) ABSTRACT

An implantable revision device includes a motion restrictor configured to substantially restrict motion of a previously implanted motion preservation disc. The motion restrictor may have a substantially incompressible portion including an upper surface configured to abut an upper plate of a previously implanted motion preservation disc and including a lower surface configured to abut a lower plate of the previously implanted motion preservation disc.

20 Claims, 5 Drawing Sheets

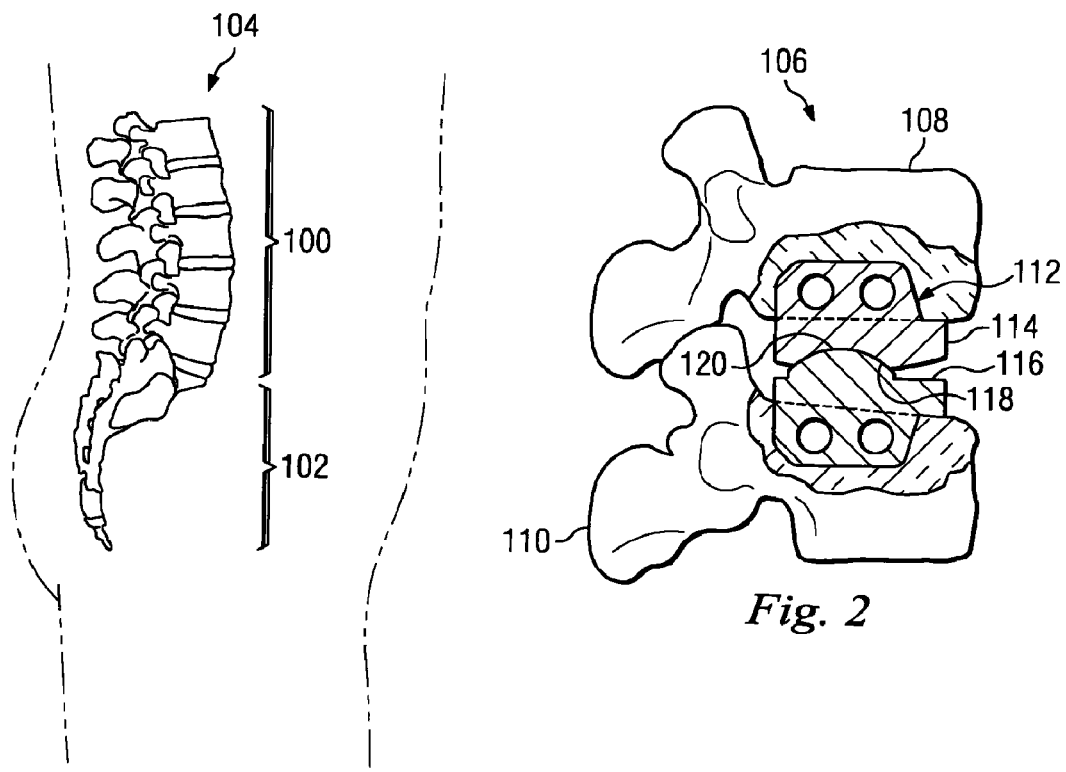
Fig. 1
Fig. 2
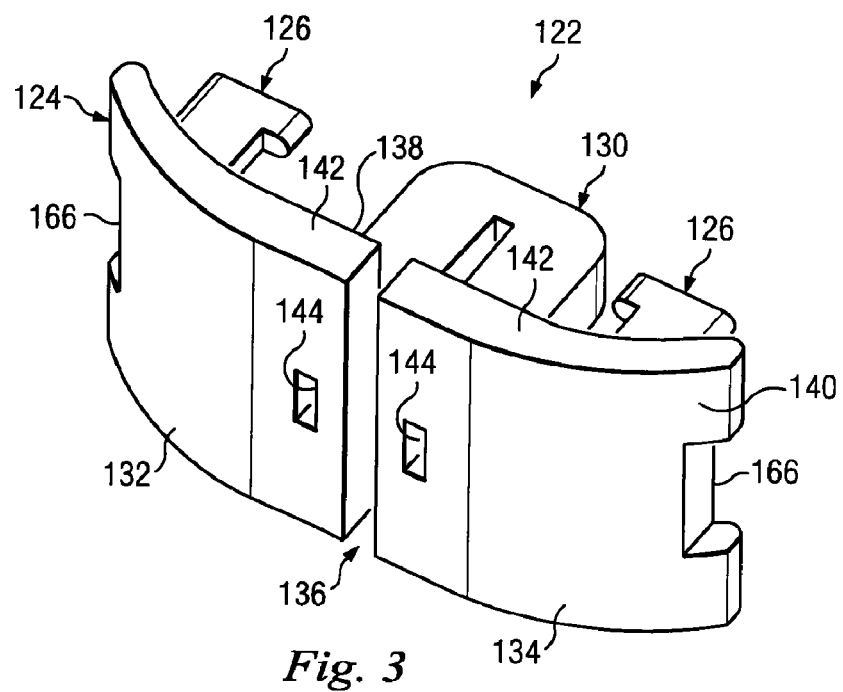
Fig. 3

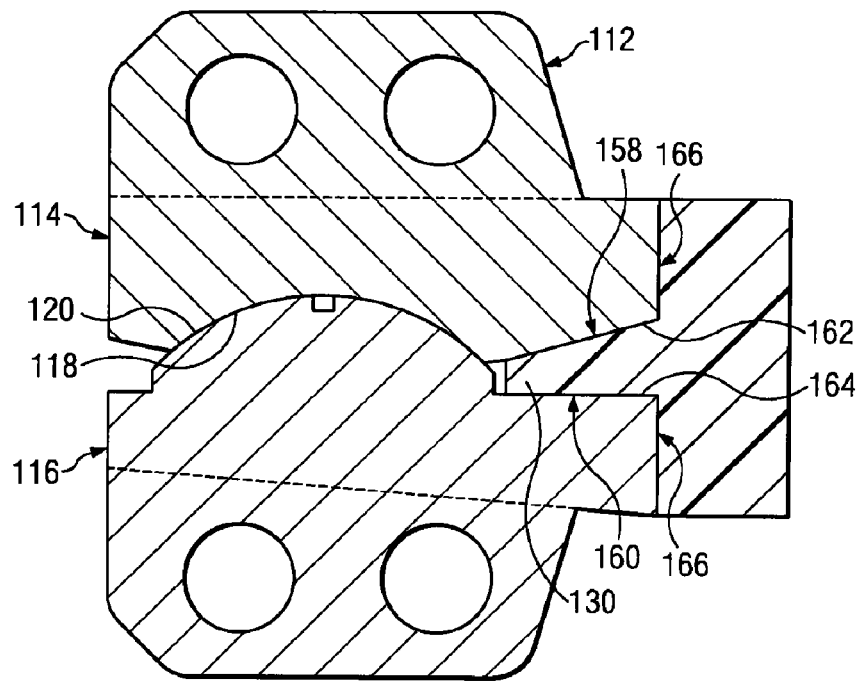
*Fig. 7*
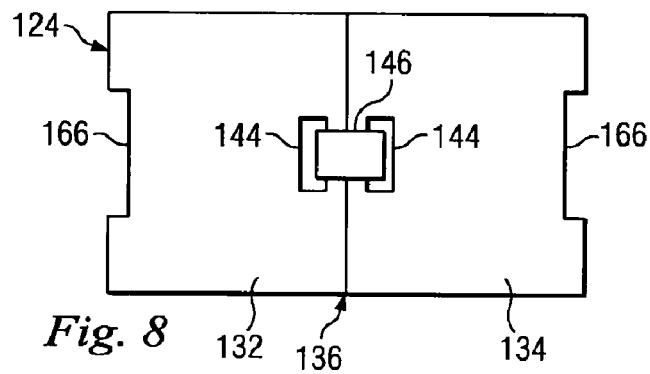
*Fig. 8*
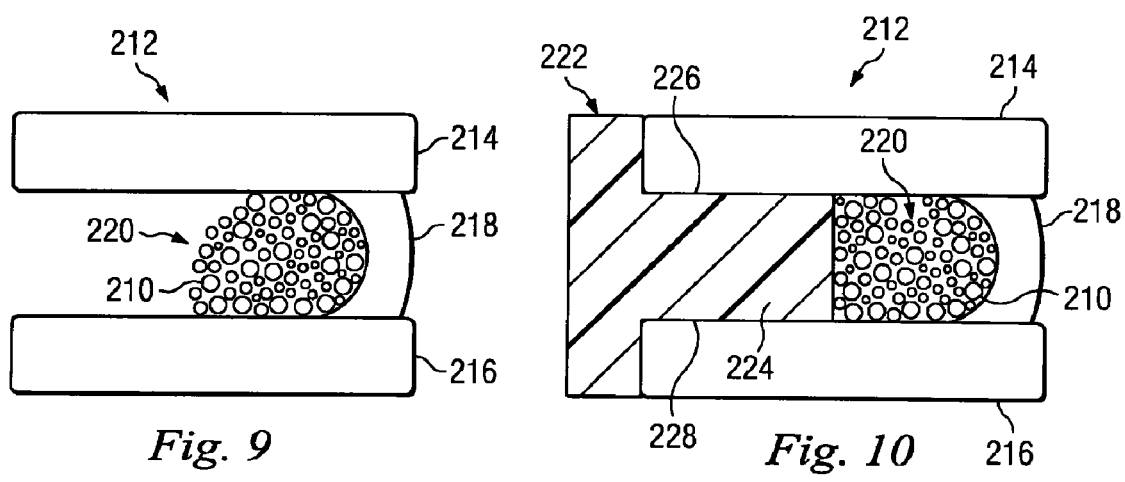
*Fig. 9*   *Fig. 10*

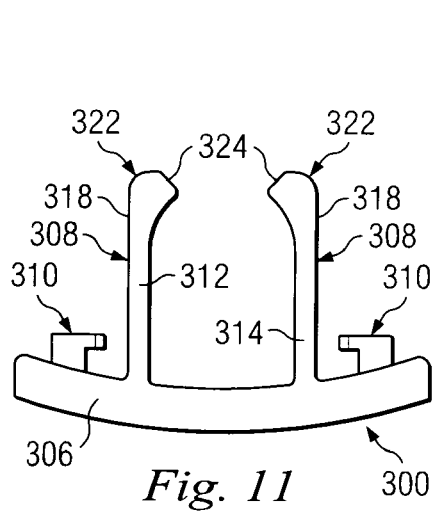
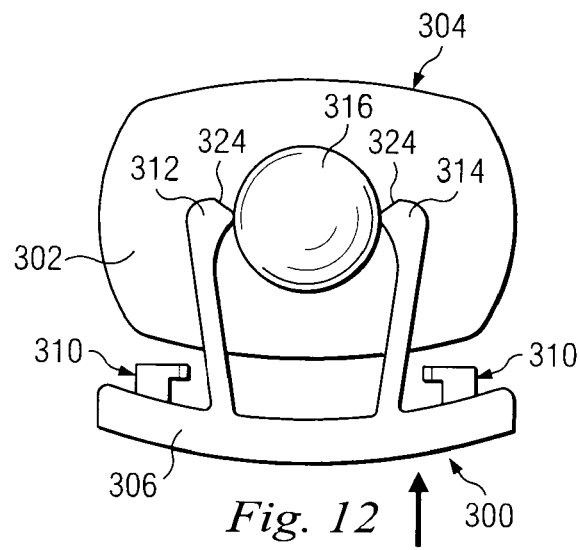
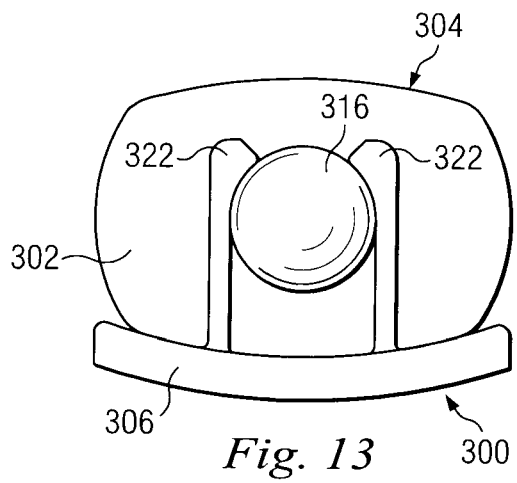
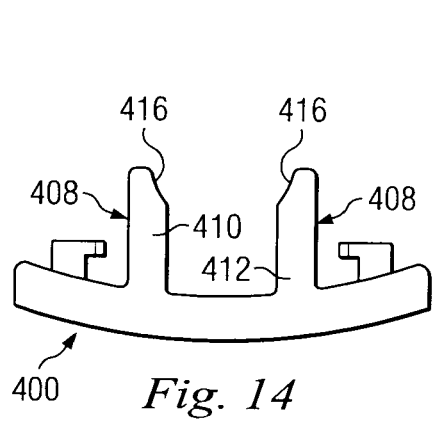
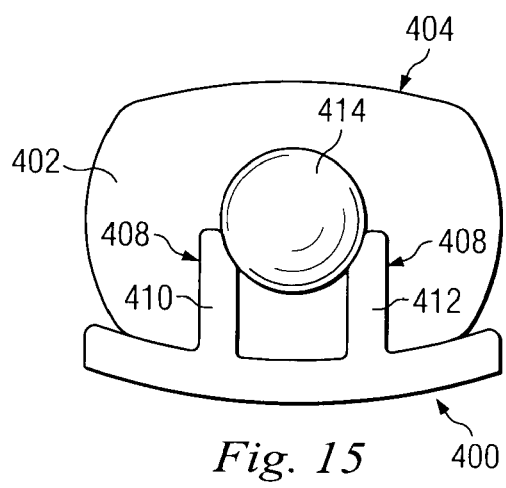

REVISION DEVICE

BACKGROUND

Spinal discs between the endplates of adjacent vertebrae in a spinal column of the human body provide critical support between the adjacent vertebrae. These discs can rupture, degenerate and/or protrude due to injury, degradation, disease or the like to such a degree that the intervertebral space between adjacent vertebrae collapses as the disc loses at least a part of its support function. This can cause impingement of the nerve roots and severe pain. In some cases, surgical correction may be required.

Typically, the surgical correction includes the removal of the natural spinal disc from between the adjacent vertebrae and, in order to preserve the intervertebral disc space for proper spinal-column function, a motion and alignment preserving prosthetic device can be inserted in the intervertebral space between the adjacent vertebrae. In this context, the motion and alignment preserving prosthetic device may be referred to as a motion preservation disc.

In some cases, the inserted motion preservation disc may not function properly for any of a wide variety of reasons including, for example, failure of or damage to the artificial disc, poor tissue healing, the deterioration of the function and/or shape of the spinal column after the surgical correction, end plate or implant subsidence, pain, and/or other patient-related factors. In response, revision surgery, that is, another surgical correction may be required in which the motion preservation disc is removed from the intervertebral space between the adjacent vertebrae. After removal of the disc, a replacement implant, typically a fusion-type implant, may be introduced to the intervertebral space.

Removal of an existing motion preservation disc can be traumatic and painful for a patient. For example, it may require portions of bone to be re-sected, which in some cases may impair the structural integrity of the joint. In other cases, removal may disturb the alignment required for proper fusion.

Although there continue to be improvements made to motion preservation disc implants and to revision techniques, a need remains for a device that can restrict the motion of previously implanted motion preservation discs while limiting patient trauma.

SUMMARY

In one exemplary aspect, this disclosure is directed to an implantable revision device including a motion restrictor configured to substantially restrict motion of a previously implanted motion preservation disc. The motion restrictor may have a substantially incompressible portion including an upper surface configured to abut an upper plate of a previously implanted motion preservation disc and including a lower surface configured to abut a lower plate of the previously implanted motion preservation disc.

In some aspects, the device may have a rigid single body or a multi-part body extending from an end of the motion restrictor. The body may be disposed substantially exterior of the upper and lower endplates. The body may also be configured with engaging elements which are configured to engage tool engaging portions on the motion preservation disc with a friction fit. The body may also be divided by a slot into first and second body parts. The slot may allow the body parts to be compressed resulting in a locked condition which could be maintained by inserting a locking member into locking apertures in the body parts.

In another exemplary aspect, this disclosure is directed to an implantable revision device configured with a motion restrictor with limiter arms. In some aspects, these may extend on opposing sides of an articulating core of the previously implanted motion preservation disc and engage the core. The motion restrictor could also have a wedge-shaped or angled profile.

In yet another exemplary aspect, this disclosure is directed to a method of revision surgery. The method may include accessing a previously implanted motion preservation disc and introducing the revision device to the previously implanted motion preservation disc. The revision device may have a substantially incompressible portion that substantially restricts the motion of the disc. The method also discloses the option of packing open spaces between the device and disc with bone graft material.

BRIEF DESCRIPTION OF THE DRAWINGS

FIG. 1 is a pictorial representation of a side elevation view of an adult human vertebral column.

FIG. 2 is a pictorial representation of a partial side view of a portion of the column of FIG. 1, depicting an exemplary motion preservation disc inserted between two adjacent vertebrae.

FIG. 3 is a pictorial representation of an isometric view of an exemplary implantable revision device.

FIG. 7 is a pictorial representation of a cross-sectional, side view of the exemplary implantable revision device shown fully engaged with a motion preservation disc.

FIG. 8 is a pictorial representation of a back view of the exemplary implantable revision device in a compressed or locked condition.

FIGS. 9 and 10 are pictorial representations showing engagement of the exemplary implantable revision device with another exemplary motion preservation disc.

FIG. 11 is a pictorial representation of a top view of an exemplary implantable revision device according to another embodiment of the present disclosure.

FIG. 12 is a pictorial representation of a top view of the exemplary implantable revision device of FIG. 11, shown being engaged around the articulating core of a motion preservation device.

FIG. 13 is a pictorial representation of a top view as in FIG. 12, showing the implantable revision device fully engaged around the articulating core of a motion preservation device.

FIG. 14 is a pictorial representation of a top view of an exemplary implantable revision device according to another embodiment of the present disclosure.

FIG. 15 is a pictorial representation of a top view of the revision device of FIG. 14, shown engaged with a motion preservation device.

DETAILED DESCRIPTION

Figure 4:
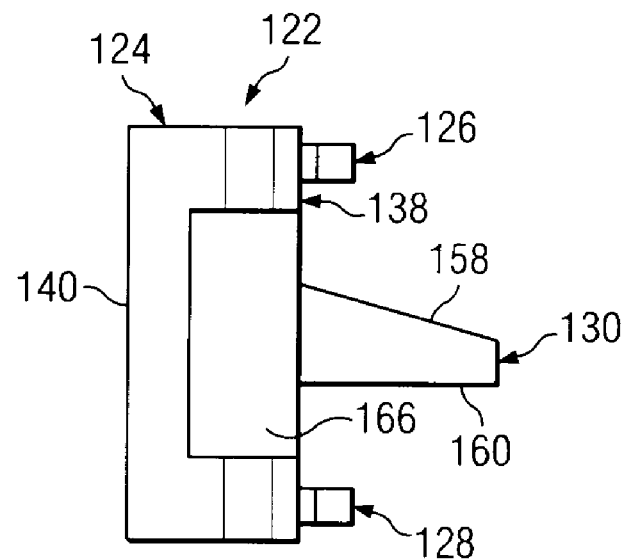
FIG. 4 is a pictorial representation of a side view of the exemplary implantable revision device of FIG. 3.

This disclosure relates generally to an implantable revision device for restricting motion of a previously implanted motion preservation prosthetic disc. For the purposes of promoting an understanding of the principles of the revision device, reference will now be made to embodiments or examples illustrated in the drawings and specific language will be used to describe the same. It will nevertheless be understood that no limitation of the scope of the invention is thereby intended. Any alterations and further modifications of the described embodiments and any further applications of the principles of the invention as described herein are contemplated as would normally occur to one skilled in the art to which this disclosure relates.

The revision device disclosed herein may be used to restrict motion, including eliminate motion, of a previously implanted motion preservation prosthetic disc. It may, for example, engage or cooperate with components of the motion preservation disc to restrict their relative movement, and thereby restrict the disc motion. So doing may, in effect, change the properties of the motion preservation disc from motion preserving to more closely mimic those of a fusion disc. The revision device may, in some examples, engage or abut against inner surfaces of upper and lower endplates of the motion preservation disc to restrict their relative movement. In other examples, the revision device may engage edges of the endplates and may cooperate with apertures in the endplate to securely connect to and restrict motion of the motion preservation disc. A locking member may assist with connecting the revision device to the motion preservation disc.

FIG. 1 illustrates schematically the lumbar spinal region 100 and the sacrum region 102 of a healthy, human spinal column 104. The spinal regions are made up of vertebrae separated by intervertebral discs. A joint comprises two adjacent vertebrae separated by an intervertebral disc. Although the illustration generally depicts the lumbar and sacrum regions, it is understood that the devices, systems, and methods of this disclosure may also be applied to all regions of the vertebral column, including the cervical and thoracic regions.

FIG. 2 shows an exemplary vertebral joint 106 including an upper vertebra 108 and a lower vertebra 110. A motion preservation disc 112, shown in cross-section, is disposed between the upper and lower vertebrae 108, 110 and may be configured to provide motion to the vertebral joint 106. The disc 112 is essentially comprised of an upper plate 114 and a lower plate 116 and in this example is an articulating ball-joint type disc. The upper plate 114 includes an articulating surface 118 formed as a recess, and the lower plate 116 includes an articulating surface 120 formed as a protruding ball. In one example, the disc 112 may include many of the features of the discs shown and described in U.S. Pat. No. 6,740,118, incorporated herein in its entirety by reference.

Figure 5:
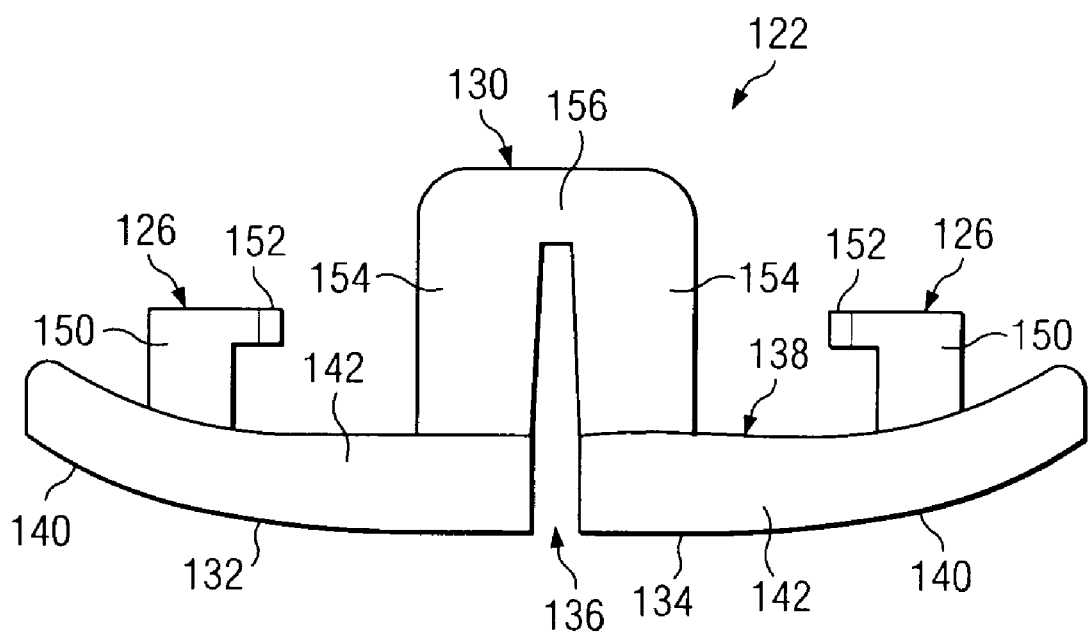
FIG. 5 is a pictorial representation of a top view of the exemplary implantable revision device FIG. 3.

FIGS. 3-5 show one exemplary embodiment of an implantable revision device 122 configured to cooperate with a motion preserving disc, such as the disc 112, to restrict motion of the motion preserving disc. The revision device 122 includes a rigid body 124, upper and lower engagement elements 126, 128, and a motion restrictor 130. The rigid body 124 supports the motion restrictor 130. When the device 122 is associated with a previously implanted disc, such as the disc 112, the motion restrictor may extend between the upper and lower plates and the engaging elements 126 and 128 may help secure the revision device 122 in place.

The rigid body 124 may include a first body portion 132 and a second body portion 134 separated by a slot 136. As explained further below, the slot 136 allows the first and second body portions 132 and 134 to be compressed together to attach to the motion preservation disc 112.

The first and second body portions 132, 134 may include an interfacing surface portion 138 that is configured to interface with the motion preservation disc 112, an opposite exterior surface 140, and outer edges 142. Shaped to fit flush with a side of the motion preserving disc 112, the interfacing surface portion 138 may have any surface shape or curvature. In the example shown the interfacing surface portion 138 is concavely arced to interface with an arced edge of the upper and lower plates 114, 116 of the disc 112. In other examples, the interfacing surface portion is planar, convex, or has other shaped surface features.

The exterior surface 140 may include locking apertures 144 configured to receive a locking member 146 (shown in FIG. 6 and described further below). In the embodiment shown, the locking apertures 144 are symmetrically formed on opposite sides of the slot 136.

The first and second body portions 132, 134 of the revision device 122 may also include insertion-tool interfaces 166 formed therein. These interfaces 166 may be configured to cooperate with an insertion tool (not shown) for use when implanting the device 122. In the embodiment shown, the interfaces 166 are reliefs or cut-outs formed in the outer edges 142 of the first and second body portions 132, 134. However, other embodiments of the revision device may employ insertion tool interfaces shaped as slots, grooves, protrusions, holes, apertures, and the like, that may be formed in the exterior surface 140 of the device. Other types of tool-engaging portions also are contemplated.

The upper and lower engaging elements 126, 128 protrude from the interfacing surface portion 138 of the rigid body 124. These upper and lower engaging elements 126, 128 are configured to respectively engage the upper and lower plates 114, 116 of the motion preservation disc 112. In this exemplary embodiment, the engaging elements 126, 128 include a rectangular-shaped base 150 and a prong 152. In alternative embodiments, the engaging elements include only a base, or alternatively, the prong may be arrow-shaped or have other shaped features. In other embodiments, the prongs may extend in directions other than that shown, such as a direction opposite that shown. Also, in some embodiments, the base 150 is cylindrical, conical, or otherwise shaped.

The motion restrictor 130 extends from the interfacing surface portion 138 of the rigid body 124. Having a U-shape, the exemplary motion restrictor 130 includes two arms 154 and a connecting bridge 156. The arms 154 each extend from one of the first and second body portions 132, 134 and are connected by the connecting bridge 156, spanning the slot 136 between the body portions 132, 134. Accordingly, the shape of the motion restrictor 130 may provide some leaf-spring like support to affect the width of the slot 136.

Configured to fit between and interface with upper and lower plates of a motion preservation disc, such as disc 112, the arms 154 and connecting bridge 156 include an upper surface 158 and a lower surface 160. As best seen in the side view of FIG. 4, the upper and lower surfaces 158, 160 are planar, but non-parallel, forming a wedge shape. In other embodiments, the upper and lower surfaces are parallel to each other, and in others, the upper and lower surfaces are non-planar. The angle formed between the upper and lower surfaces, as well as the surface features, may be defined by features of the upper and lower endplates of a corresponding motion preservation disc.

At least a portion of the motion restrictor 130 may be substantially incompressible under normal spinal loads applied at the upper and lower surfaces 158, 160 and may be formed of any suitable biocompatible material including, for example, metals such as cobalt-chromium alloys, titanium alloys, nickel titanium alloys, and/or stainless steel alloys. In one embodiment, the motion restrictor 130 is formed of a cobalt-chrome-molybdenum metallic alloy (ASTM F-799 or F-75). Ceramic materials such as aluminum oxide or alumina, zirconium oxide or zirconium, compact of particulate diamond, and/or pyrolytic carbon may also be suitable. Polymer materials may also be used, including any member of the polyaryletherketone (PAEK) family such as polyetheretherketone (PEEK), carbon-reinforced PEEK, or polyetherketoneketone (PEKK); polysulfone; polyetherimide; polyimide; ultra-high molecular weight polyethylene (UHMWPE); and/or cross-linked UHMWPE, among others. In some embodiments, different features, such as the body and the motion restrictor, are formed of different materials. In other embodiments, the entire device 122 is integrally formed of a single material.

Figure 6:
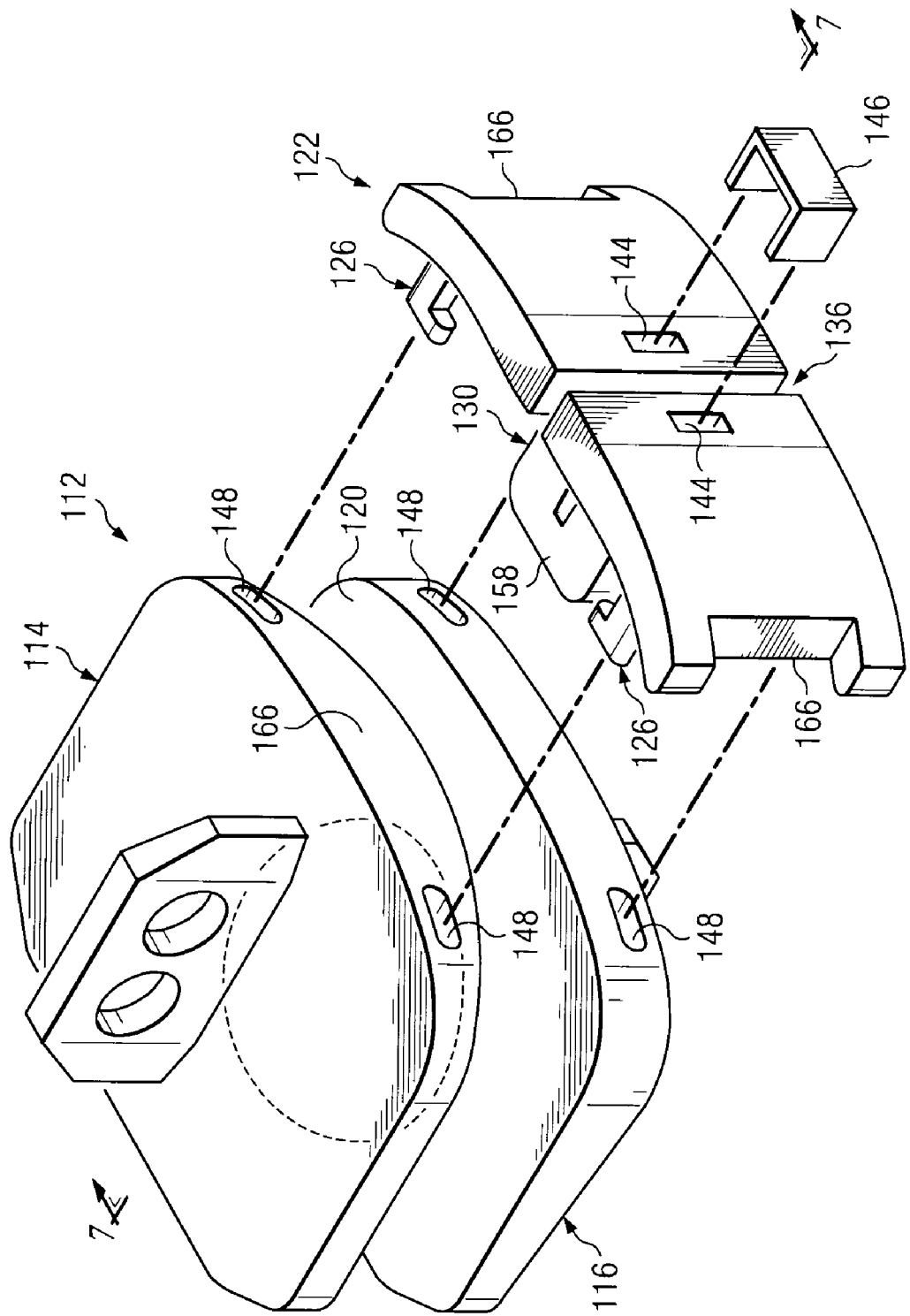
FIG. 6 is a pictorial representation of an isometric view of the exemplary implantable revision device shown in relation to an exemplary motion preservation disc.

FIGS. 6-8 show the revision device 122 in association with the exemplary motion preservation disc 112. FIG. 6 shows an exploded view with the revision device in an unlocked condition, FIG. 7 shows an off-center cross-sectional view, taken along lines 7-7 in FIG. 6, and FIG. 8 shows a back view of the revision device in a locked condition. As shown in these figures, the upper plate 114 of the motion preservation disc 112 includes an inwardly facing lower surface 162 and the lower plate 116 includes an inwardly facing upper surface 164. The upper and lower plates 107, 108 also include tool engaging portions 148 formed therein. These may be configured to cooperate with an insertion tool for use when implanting the disc 112. In the embodiment shown, the tool engaging portions 148 are apertures formed in the edges of the plates 114, 116. However, other motion preservation discs may employ tool engaging portions shaped as slots, grooves, protrusions, and the like.

When the revision device 122 is introduced to the previously implanted disc 112, the upper and lower engaging elements 126, 128 may engage the tool engaging portions 148. At the same time, the upper and lower surfaces 158, 160 of the motion restrictor 130 engage or abut against the respective lower surface 162 of the upper plate 114 and the upper surface 164 of the lower plate 116 of the disc 112. As best seen in FIG. 7, the shape of the motion restrictor 130 corresponds with the shape and design of the motion preservation disc 112.

FIGS. 6 and 8 show a locking member 146 configured to interface with the locking apertures 144 to hold the body 124 in a locked condition so that the device 122 is maintained on the disc 112 as described further below. In this embodiment, the locking member 146 is shaped as a staple and may be configured to span the slot 136 and engage with both the first and second body portions 132, 134. In other embodiments, the locking member may be, for example, a bracket, an anchor, or other component capable of assisting in maintaining the revision device 122 on the motion preservation disc 112.

In use, a previously implanted motion preservation disc, such as the disc 112 is accessed in a patient. In order to restrict motion of the disc 112 without removing it from the patient, the revision device 122 is introduced to the disc 112 in an unlocked condition and once place, maintained in a locked condition to lock or secure the revision device 122 on the disc 112. Introducing the device may include engaging the rigid body 124 to the disc 112 using the upper and lower engaging features 126, 128 that may engage features of the disc 112, such as the tool engaging portions 148, to help secure the device 122 in place on the disc 112. While introducing the engaging features 126, 128, the motion restrictor 130 is likewise introduced between the upper and lower endplates to engage or abut against the inner surfaces of the endplates.

Once introduced to the disc 112, an insertion tool (not shown) may be used to manipulate the device from its unlocked condition (as in FIG. 6) to its locked condition (as in FIG. 8). The insertion tool also may grip the device 122 at the insertion tool interfaces 166 and squeeze the device 122 to move the body portions 132, 134 closer together, causing deformation about connecting bridge 156 and decreasing the width of the slot 136. This relative movement of the body portions 132, 134 also moves the engaging elements 126, 128 closer together, squeezing the engaging elements against inner surfaces of the tool engaging portions 148 of the disc 112, effectively frictionally locking the device 122 to the disc 112, and thereby placing the device in the locked condition. While applying the squeezing force to the body portions 132, 134, the locking member 146 is introduced into the locking apertures 144 to maintain the rigid body in the locked condition, as shown in FIG. 8. Thus, when locked in place, the motion restrictor 130 substantially restricts articulation of the disc 112 in at least one direction, and the engaging elements 126, 128 substantially restrict articulation in other directions.

In some embodiments, the rigid body 124 and engaging elements 126, 128 are used without the motion restrictor 130 to securely attach to the upper and lower endplates 114, 116 of the motion preservation disc 112. In these embodiments, movement of the plates 114, 116 relative to one another is restricted by the strength of the rigid body 124 and corresponding engaging elements 126, 128. By restricting motion of the plates 114, 116 relative to each other, this also restricts motion of the motion preservation disc 112.

In some embodiments, the tool engaging portions on the motion preservation disc is formed with inner features that may receive the prongs 152. In these embodiments, when the revision device is in the locked condition, it is not frictionally engaged, but may be locked on the motion preservation disc through physical interference that blocks removal of the engaging features from the tool engaging portions.

Some methods of revision surgery also incorporate implanting a bone grafting material 210 along with the revision device 122. For example, FIGS. 9 and 10 show an exemplary motion preservation disc 212 including cantilevering upper and lower plates 214, 216 connected by a motion preserving connecting piece 218. Although not shown, the endplates 214, 216 also include apertures that allow vascularization and bone growth through the plates 214, 216. The plates 214, 216 form a hollow center 220.

During revision surgery, the disc 212 may be packed with bone graft material, tissue, or other osteogenic materials that promote bone growth, as best seen in FIG. 9. Osteogenic materials include, without limitation, autograft, allograft, xenograft, demineralized bone, synthetic and natural bone graft substitutes, such as bioceramics and polymers, and osteoinductive factors. A separate carrier to hold materials within the disc can also be used. These carriers can include collagen-based carriers, bioceramic materials, such as BIO-GLASS®, hydroxyapatite and calcium phosphate compositions. The carrier material may be provided in the form of a sponge, a block, folded sheet, putty, paste, graft material or other suitable form. The osteogenetic compositions may include an effective amount of a bone morphogenetic protein, transforming growth factor $\beta 1$, insulin-like growth factor 1, platelet-derived growth factor, fibroblast growth factor, LIM mineralization protein (LMP), and combinations thereof or other therapeutic or infection resistant agents, separately or held within a suitable carrier material.

After introducing the bone grafting material 210, a revision device 222 may be introduced to the disc 212 to restrict motion between the plates 214, 216 using the methods and techniques described above. The revision device 222 may include any of the features described with respect to other embodiments, but in this embodiment, the revision device 222 includes a motion restrictor 224 having substantially parallel upper and lower surfaces 226, 228. These may be configured to engage or abut against the upper and lower places 214, 216. The revision device 222 may secure the bone grafting material within the disc and restrict motion of the disc and over time, the disc 212 may become fused to the adjacent vertebrae, thereby changing the motion preservation disc into a fusion type device.

FIGS. 11-13 show another embodiment of a revision device 300. A top view of the revision device 300 is shown in FIG. 11 and FIGS. 12 and 13 show top views of the revision device 300 being inserted onto a lower plate 302 of a motion preserving disc 304. For purposes of explanation, the upper plate of the motion preservation disc 304 is not shown.

The revision device 300 may include any of the features of the other revision device embodiments described herein, including a rigid body 306, a motion restrictor 308, upper engaging elements 310, and lower engaging elements (not shown). In this embodiment, the rigid body 306 is a single solid component, rather than having separate body portions as described above with reference to the device 122.

The motion restrictor 308 includes a first limiter arm 312 and a second limiter arm 314. The limiter arms 312 and 314 can function to fit between and engage or abut inner surfaces the upper and lower endplates of the disc 304. By so doing, the limiter arms 312, 314 can restrict relative movement of the upper and lower endplates of the motion preservation disc 304. In some embodiments, the limiter arms 312, 314 are formed to elastically deform to fit around features of the disc 304, such as the articulating core 316, shown in FIG. 12. Nevertheless, they may be substantially incompressible under normal spinal loads applied at the upper surface and lower surface of the motion restrictor 308 in order to restrict motion of the disc 304.

In the embodiment shown, the limiter arms 312 and 314 may include ends 322 having tapered leading portions 324. These leading portions 324 are configured to contact and slide against opposing sides of the articulating core 316, forcing the limiter arms 312, 314 apart, as best seen in FIG. 12. The arms 312 and 314 spread by flexing in relation to the rigid body 306. As the leading portions 324 pass beyond opposing sides of the core 316, they close around the articulating core 316 as shown in FIG. 13, securely holding the device 300 in place and restricting motion of the disc 304. In some embodiments the engaging elements 310 are not included and the motion restrictor 308 alone secures the revision device 300 to the disc 304.

It should be noted that in some embodiments, separation of the arms to receive or extend around the core 316 occurs at the body 306. In some of these embodiments, the body 306 may be elastically flexed to move the ends 322 of the arms 312, 314 apart and then fit them around the core 316. In other embodiments, the ends 322 of the arms 312, 314 are sized to connect about and enclose the core 316. Other configurations also are contemplated.

An additional embodiment of a motion restrictor 400 is shown in FIGS. 14 and 15. A top view of the revision device 400 is shown in FIG. 14, while FIG. 15 shows a top view of the revision device 400 in place on a lower plate 402 of a motion preserving disc 404. Again, for purposes of explanation, the upper plate of the motion preservation disc 404 is not shown.

The revision device 400 may include any of the features of the other revision device embodiments described herein, and includes a motion restrictor 306 having a first limiter arm 410 and second limiter arm 412 which extend up to, but do not encompass the articulating core 414. In this embodiment, the limiter arms 410 and 412 are shown with contoured interfaces 416 which are configured to match the articulating core 414. This embodiment is pressed onto the disc 404 until the interfaces 416 of the limiter arms 410 and 412 engage the articulating core 414.

Although the shown exemplary motion preservation discs include either a ball-shaped core or a cantilever-type motion disc, these are only shown as examples of types of motion mechanisms. It is contemplated that those skilled in the art will readily see the application of this device to other discs having motion preservation features constructed other than those shown; such as, for example, mechanical springs, nucleus replacement, elastic material and so forth. In addition, In other embodiments, the engaging elements 126, 128 do not engage insertion-tool interfaces, but are configured to cooperate with other features on the previously implanted motion preservation disc.

Although shown and described as being used in an articulation disc having one articulation interface, principles of the present invention could be used to restriction motion of a motion preservation disc having two articulation surfaces, such as with discs that employ a nucleus and two endplates. In some embodiments, the revision device does not include locking apertures that receive a locking member. In some embodiments, for example, the locking member may extend from edges of the revision device, such as from the insertion-tool interfaces, to secure the revision device in a locked condition.

Although only a few exemplary embodiments have been described in detail above, those skilled in the art will readily appreciate that many modifications are possible in the exemplary embodiments without materially departing from the novel teachings and advantages of this disclosure. Accordingly, all such modifications and alternative are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure. It is understood that all spatial references, such as "horizontal," "vertical," "top," "upper," "lower," "bottom," "left," "right," "cephalad," "caudal," "upper," and "lower," are for illustrative purposes only and can be varied within the scope of the disclosure. In the claims, means-plus-function clauses are intended to cover the elements described herein as performing the recited function and not only structural equivalents, but also equivalent elements.

I claim:

1. A system for creating a fusion device in an intervertebral disc space, the system comprising:
   an implantable motion preservation disc disposed in the intervertebral disc space, the motion preservation disc having an upper plate with an upper surface that interfaces with the upper vertebral body and a lower plate with a lower surface that interfaces with the lower vertebral body, the motion preservation disc being structurally configured to provide relative motion to the upper and lower vertebral bodies that at least partially matches motion of a normal natural intervertebral disc;
   a motion restrictor structurally arranged to convert the motion preservation disc into a fusion structure by eliminating motion capability of the motion preservation disc, the motion restrictor structurally arranged to be substantially incompressible in a vertical direction, the motion restrictor including an upper surface configured to abut the upper plate of the motion preservation disc and including a lower surface configured to abut the lower plate of the motion preservation disc, the motion restrictor being configured to substantially eliminate motion of the motion preservation disc; and a rigid body at an end of the motion restrictor, the motion restrictor extending from a substantially central location on the rigid body, the body being configured to be disposed substantially exterior of the upper and lower endplates when the motion restrictor is implanted on the implantable motion preservation disc, wherein the rigid body includes a first body portion connected to a first half of the motion restrictor and a second body portion connected to a second half of the motion restrictor, the first body portion and the second body portion being separated by a slot that extends into the motion restrictor, the revision device motion restrictor further comprising engaging elements connected to the first and second body portions and being configured to engage tool engaging portions on the motion preservation disc.

2. The system of claim 1, wherein the motion restrictor is configured to allow the first and second body portions to displace from a locked condition to an unlocked condition.

3. The system of claim 2, further comprising a locking member, wherein the first and second body portions each include a locking aperture configured to receive the locking member to secure the first and second body portions in the locked condition.

4. The system of claim 1, wherein the motion restrictor is U-shaped.

5. The system of claim 1, wherein the engaging elements are spaced from upper and lower surfaces of the rigid body.

6. The system of claim 1, further comprising:
an upper engaging element protruding from the rigid body and being configured to engage the upper plate of the motion preservation disc; and
a lower engaging element protruding from the rigid body and being configured to engage the lower plate of the motion preservation disc.

7. The system of claim 1, wherein the motion restrictor is configured to extend on opposing sides of an articulating core of the previously implanted motion preservation disc.

8. The system of claim 1, wherein the motion restrictor includes a first limiter arm and a second limiter arm that extend between the upper and lower plates of the previously implanted motion preservation disc.

9. The system of claim 1, wherein the motion restrictor is wedge shaped.

10. An implantable revision device system for creating a fusion device from a nonfunctioning, nonfusion previously implanted motion preservation disc disposed in the intervertebral disc space, the implantable revision device system comprising:
a nonfunctioning, non fusion, previously implanted motion preservation disc, the motion preservation disc having an upper plate with an upper surface that interfaces with the upper vertebral body and with a lower surface facing away from the upper surface of the upper plate and a lower plate with a lower surface that interfaces with the lower vertebral body and with an upper surface facing away from the lower surface of the lower plate, the lower surface of the upper plate opposing the upper surface of the lower plate, the nonfunctioning, nonfusion motion preservation disc being structurally configured to provide relative motion to the upper and lower vertebral bodies that at least partially matches motion of a normal natural intervertebral disc; and
a revision device configured to substantially eliminate motion of the previously implanted motion preservation disc, the revision device comprising a rigid body and a motion restrictor protruding from the rigid body, the motion restrictor including an upper surface and a lower surface and being configured to extend into the previously implanted motion preservation disc such that the upper surface of the motion resistor abuts the lower surface of the upper plate of the motion preservation disc and the lower surface of the motion resistor abuts the upper surface of the lower plate of the motion preservation disc;

wherein the rigid body includes a first body portion and a second body portion separated by a slot, the first and second body portions being connected to the motion restrictor such that when the motion restrictor elastically flexes in the lateral direction, the first and second body portions move relative to each other, the first body portion including the upper and lower engaging elements, the second body portion including a second upper engaging element and a second lower engaging element, further comprising a locking member, wherein the first and second body portions each include a locking aperture configured to receive the locking member to secure the first and second body portions in the locked condition.

11. The implantable revision device system of claim 10, wherein the motion restrictor is wedge shaped.

12. The implantable revision device system of claim 10, wherein the motion restrictor is configured to extend on a single side of an articulating core of the previously implanted motion preservation disc.

13. The implantable revision device system of claim 10, wherein the upper and lower engaging elements are configured to engage tool engaging portions on the previously implanted motion preservation disc.

14. The implantable revision device system of claim 10, wherein the motion restrictor is U-shaped.

15. An implantable revision device system for creating a fusion device from a nonfunctioning, nonfusion previously implanted motion preservation disc disposed in the intervertebral disc space, the implantable revision device system comprising:
a nonfunctioning, non fusion, previously implanted motion preservation disc, the motion preservation disc having an upper plate with an upper surface that interfaces with the upper vertebral body and with a lower surface facing away from the upper surface of the upper plate and a lower plate with a lower surface that interfaces with the lower vertebral body and with an upper surface facing away from the lower surface of the lower plate, the lower surface of the upper plate opposing the upper surface of the lower plate, the nonfunctioning, nonfusion motion preservation disc being structurally configured to provide relative motion to the upper and lower vertebral bodies that at least partially matches motion of a normal natural intervertebral disc; and
a revision device configured to substantially eliminate motion of the previously implanted motion preservation disc, the revision device comprising:
a rigid body,
a motion restrictor protruding from the rigid body, the motion restrictor including an upper surface and a lower surface and being configured to extend into the previously implanted motion preservation disc such that the upper surface of the motion resistor abuts the lower surface of the upper plate of the motion preservation disc and the lower surface of the motion resistor abuts the upper surface of the lower plate of the motion preservation disc, a plurality of upper engaging elements protruding from the rigid body and being configured to engage the motion preservation disc, and a plurality of lower engaging elements protruding from the rigid body and being configured to engage the motion preservation disc, wherein the upper and lower engaging elements are configured to attach to the upper and lower plates of the motion preservation disc by friction, wherein the upper and lower engaging elements include a base and a prong extending laterally from the base.

16. The implantable revision device system of claim 15, wherein the upper and lower engaging elements are configured to engage tool engaging portions on the previously implanted motion preservation disc.

17. The implantable revision device system of claim 15, wherein the motion restrictor is U-shaped.

18. The implantable revision device system of claim 15, wherein the upper and lower engaging elements are spaced from upper and lower surfaces of the rigid body.

19. The implantable revision device system of claim 15, wherein the motion restrictor is wedge shaped.

20. The implantable revision device system of claim 15, wherein the motion restrictor is configured to extend on a single side of an articulating core of the previously implanted motion preservation disc.

* * * * *